United States Patent [19]

Kraus et al.

[11] 4,040,928

[45] Aug. 9, 1977

[54] SPECIFIC ION SENSOR AND METHOD OF MANUFACTURE

[75] Inventors: Walter R. Kraus, Centerville; David J. Kelch, Bellbrook; Gerald A. Jensen, Kettering, all of Ohio

[73] Assignee: The Mead Corporation, Dayton, Ohio

[21] Appl. No.: 378,025

[22] Filed: July 10, 1973

Related U.S. Application Data

[63] Continuation-in-part of Ser. No. 235,055, March 16, 1972, abandoned.

[51] Int. Cl.$^2$ ............................................. G01N 27/46
[52] U.S. Cl. ................................. 204/195 M; 264/113
[58] Field of Search ......................... 204/1 T, 195 M; 264/112, 113

[56] References Cited

U.S. PATENT DOCUMENTS

| | | | |
|---|---|---|---|
| 3,591,464 | 7/1971 | Frant et al. | 204/195 M |
| 3,607,710 | 9/1971 | Farren et al. | 204/195 M |
| 3,708,411 | 1/1973 | Vanslette | 204/195 M |
| 3,723,589 | 3/1973 | Kennedy | 264/113 |

*Primary Examiner*—T. Tung
*Attorney, Agent, or Firm*—Biebel, French & Nauman

[57] ABSTRACT

A specific ion sensor comprising a solid state membrane connected by a solid junction to an output terminal. The membrane has a conductive backing which is die pressed in place along with the membrane itself. An electrical lead is bonded to the conductive backing as with a conductive epoxy, and the assembly is then coated on the sides and back with an insulative coating. Thereafter the coated assembly is sealed in place within a sensor housing, and the electrical lead is connected to an appropriate output terminal mounted on the housing.

9 Claims, 8 Drawing Figures

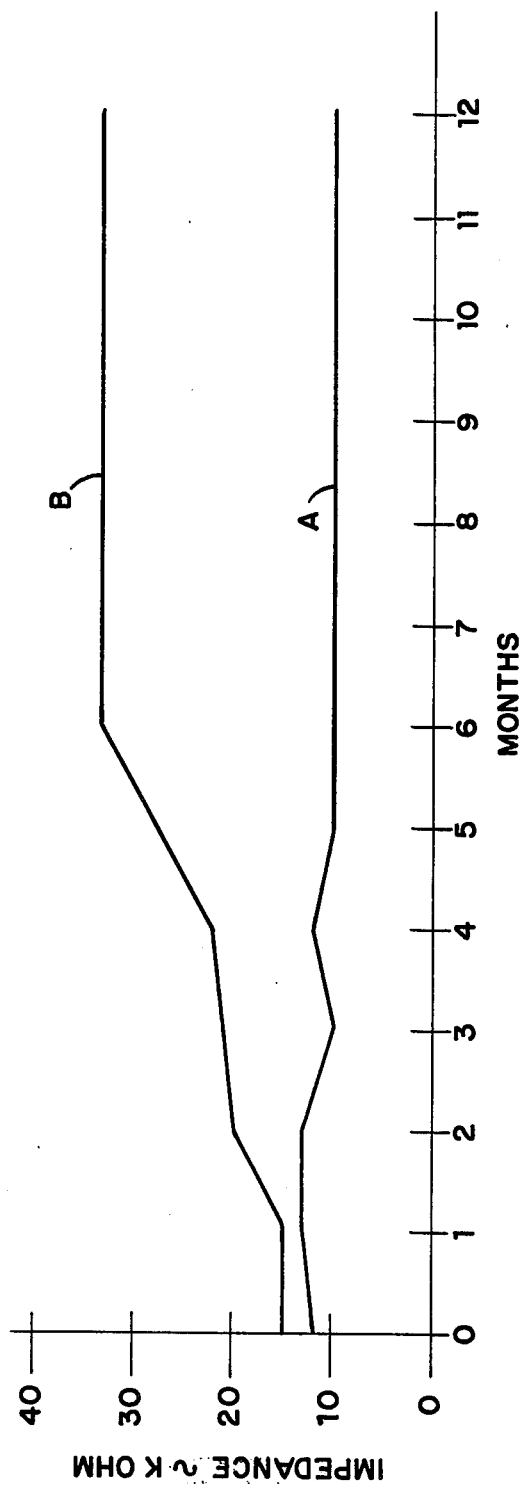
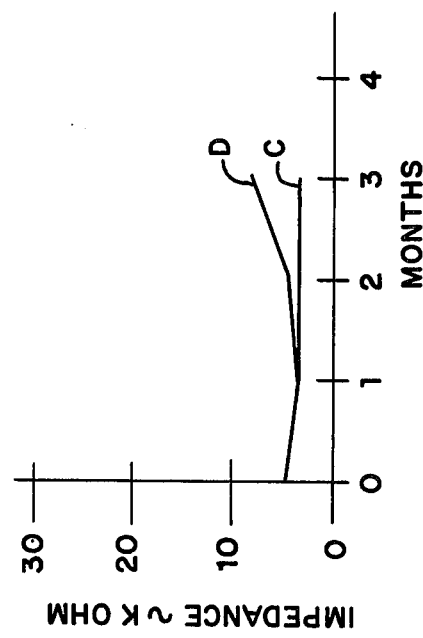

SPECIFIC ION SENSOR AND METHOD OF MANUFACTURE

CROSS REFERENCE TO RELATED APPLICATIONS

This application is a continuation-in-part of Ser. No. 235,055 filed Mar. 16, 1972, now abandoned, and is related to Ser. No. 235,116 filed Mar. 16, 1972, now U.S. Pat. No. 2,770,608.

BACKGROUND OF THE INVENTION

This invention relates to the field of specific ion sensing and more particularly to sensors comprising a solid state membrane responsive to the activity of a specific ion in a process solution. Typical prior art sensors for this purpose are disclosed in Jerrold-Jones et al. U.S. Pat. No. 3,354,069, Farren et al. U.S. Pat. No. 3,607,710, Vanslette U.S. Pat. No. 3,708,411 and Ross et al. Canadian Pat. No. 763,082. Sensors disclosed in these and other references generally provide membranes for measuring any of a number of specific ions, such as for instance sulfide, chloride, lead, silver, fluoride, and potassium. Glass membranes have been used for many years for detecting the presence of hydrogen ion.

In the usual application of prior art sensors a measuring electrode fitted with an appropriate solid state membrane (for instance a silver sulfide membrane wherein sulfide ion activity is to be measured) is immersed in a solution of unknown ion concentration together with a calomel or other reference electrode. Migration of the specific ion through the lattice structure of the solid state membrane creates a half-cell potential closely following the well known Nernst relation. Simultaneously an essentially constant half-cell potential occurs at the reference electrode, and both electrodes are connected to a high impedance electrometer. Within the measuring electrode there is usually an electrolyte solution such as for instance an aqueous saturated solution of KCL and AgCl to provide a bridge between the solid state membrane and an output terminal wire. Alternatively there may be a solid connection between the membrane and the terminal wire as shown for instance in the above mentioned Vanslette patent. The voltage difference measured by the electrometer provides a measure of the concentration or activity of the ion being sensed.

In Ser. No. 235,116 there is disclosed a process controller wherein are employed a pair of identical electrodes each fitted with a solid state membrane to detect the presence of the same type of ion. One electrode is immersed in a process solution and the other is immersed in a reference solution. An electrical bridge is provided between the solutions, and the electrode output terminals are connected to the input side of a difference amplifier. The output of the difference amplifier regulates the addition of a concentration correcting fluid to the process solution being monitored.

For applications such as process controllers of the above described type it is necessary to produce specific ion sensors characterized by rugged construction, ease of assembly, long life, high sensitivity and freedom from internal electrolyte leakage. None of the known prior art sensors has been found to be entirely satisfactory in all of these respects.

SUMMARY OF THE INVENTION

This invention provides an improved specific ion sensor wherein an ion sensing material selected from the class consisting of silver sulfide and silver bromide is backed with a relatively thick layer of metallic silver in an integral solid state membrane. The membrane is produced by die pressing a layer of powdered ion sensing material together with a layer of powdered metallic silver, so that the silver is intimately bonded to the ion sensing material with no contaminating material therebetween. An electrical output lead is attached directly to the metallic silver layer, and the membrane with the output lead attached is sealed into an appropriate housing. There is an output terminal mounted on the housing, and the output lead from the membrane is connected to this terminal. A non conductive coating may be provided to isolate the metallic silver layer and the output lead from the housing and from any process solution in contact with the front face of the membrane.

The general construction of this sensor eliminates many of the causes of failure in prior art sensors in that durability and reliability are greatly improved while at the same time achieving an exceptionally high degree of sensitivity. Moreover, it has been found that the sensor of this invention has an unexpectedly long life and that this longevity is somehow related to the process by which the membrane is produced. Such long life has not been obtained from similarly constructed sensors employing solid state membranes produced by die pressing the ion sensing material and thereafter vacuum depositing a layer of metallic silver on the back of the membrane.

Accordingly it is an object of this invention to provide a specific ion sensor of greatly increased useful life. Another object of the invention is to provide an improved method of manufacturing a specific ion sensor. Other and further objects and advantages of the invention will be apparent from the following description, the accompanying drawings, and the appended claims.

BRIEF DESCRIPTION OF THE DRAWINGS

FIG. 4 is a plot of measured impedance as observed during life testing of sensors equipped with a silver bromide membrane;
FIG. 5 is a plot of measured sensor impedance as observed during life testing of sensors equipped with a silver sulfide membrane.

DESCRIPTION OF THE PREFERRED EMBODIMENTS

Figures 1, 1A:
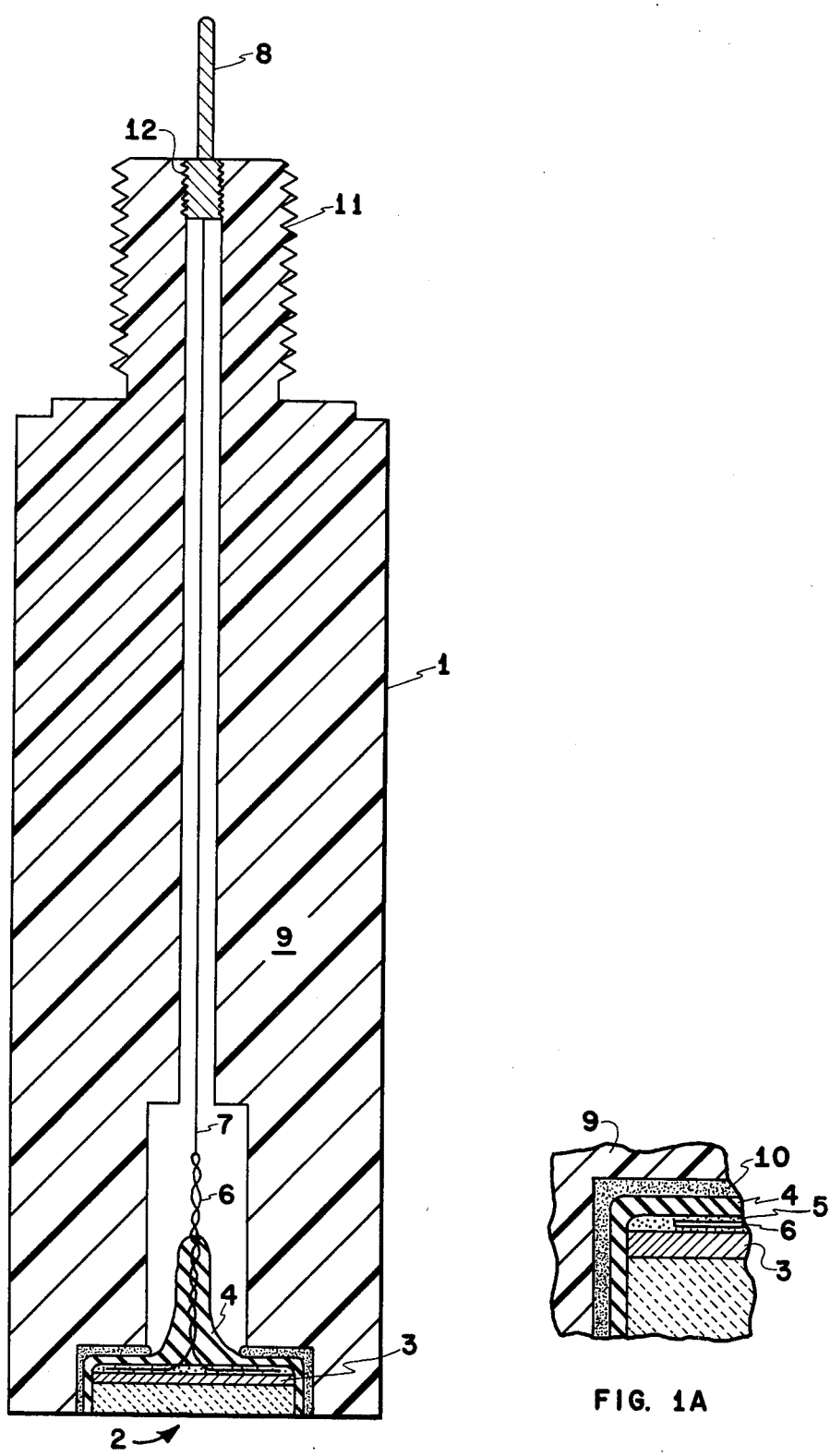
FIG. 1 is a cross section view of an assembled sensor.
FIG. 1a is an enlarged portion of FIG. 1.

A cross sectional view of a preferred embodiment of the invention is shown in FIG. 1 and in FIG. 1a which is an enlarged portion thereof. Shown therein is a sensor 1 comprising a solid state membrane 2 mounted in a housing 9. Membrane 2 has a silver backing 3 which is bonded directly to braided wires 6. Silver backing 3 is relatively thick and as described in the example below may comprise about 12 percent by weight of the total membrane.

Braided wires 6 are soldered to a stranded wire 7 which extends upwardly to pin jack 8, and pin jack 8 is threaded as at 12 for connection to housing 9. Housing 9 is also provided with threads 11 at the upper end thereof. Threads 11 enable physical attachment of sensor 1 to a measuring instrument or a process controller such as the process controller disclosed in Ser. No. 235,116. Pin jack 8 is configured for detachable connection to an electronics package within a measuring instrument of such a process controller.

Braided wires 6 are bonded to silver backing 3 by means of a conductive epoxy resin 5. This insures a good electrical connection between membrane 2 and pin jack 8. To guard against creation of any low impedance path between silver plate 3 and an external process solution, there is provided a non conductive coating 4. Coating 4 completely covers the edges of membrane 2, the edges and back surface of silver backing 3, and the lower ends of braided wires 6. The membrane subassembly comprising membrane 2, and braided wires 6, with coating 4 thereon, is bonded to housing 9 by means of an epoxy adhesive 10.

A specific ion sensor having a solid junction, solid state membrane as above described is rugged, reliable, and relatively easy to assembly. It is superior to the usual liquid junction sensor in that it eliminates the problems related to variation in junction potential, and leakage or deterioration of interal electrolyte. Moreover, the solid junction enables high temperature operation by avoiding creation of the high internal pressures which are generated when an aqueous electrolyte is subjected to high temperature.

Figure 2:
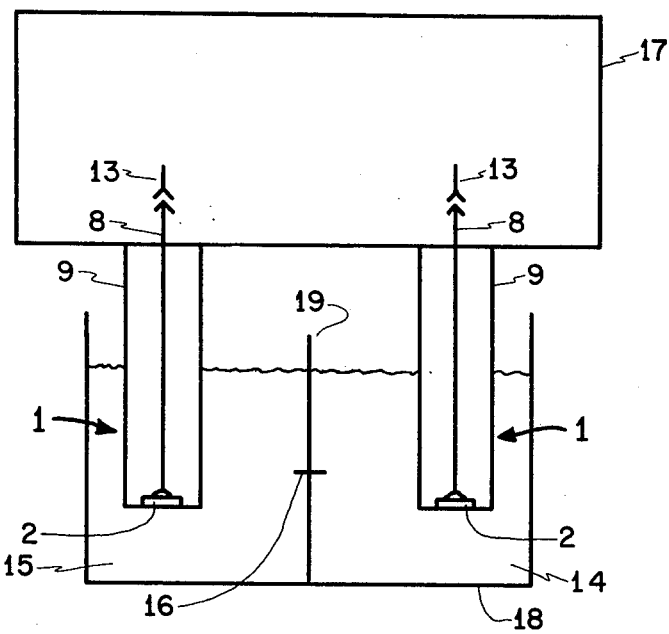
FIG. 2 is a schematic diagram of a pair of sensors as employed in a typical application.

A typical application of this invention is illustrated in FIG. 2. As shown therein a pair of identical specific ion sensors are connected to a high impedance electrometer 17 with pins 8 extending upwardly to join with electrometer connectors 13. The sensors extend downwardly into a vessel 18 divided into two compartments by a partition 19. One compartment is filled with a reference solution 14, and the other compartment is filled with a test solution 15. An electrical bridge such as a wick 16 connects the two solutions. Reference solution 14 may be, for instance, an aqueous silver nitrate solution containing a predetermined concentration of silver ions, and test solution 15 may be a sample of a process stream containing silver ions of unknown concentration. The electrical output signal generated by electrometer 17 may be used to control a solenoid valve which regulates addition of silver ions to the process stream, all as described in detail in Ser. No. 235,116.

Figure 3:
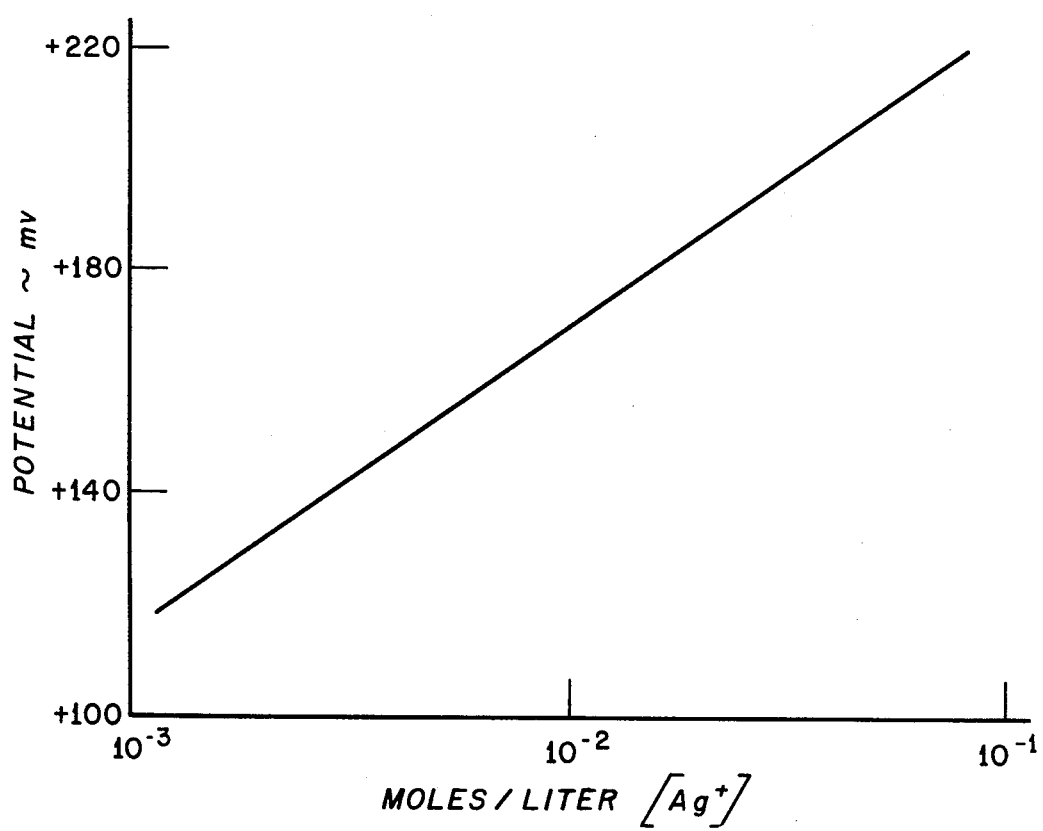
FIG. 3 is a plot of sensor response to $Ag^+$ ion in a silver nitrate solution.

For such an application, membranes 2 may be of silver sulfide construction, and will generate voltages across their respective surfaces which are related to silver concentrations in the surrounding fluids. These voltages follow the Nernst relation as illustrated in FIG. 3 for a sensor provided with a silver-backed, silver sulfide membrane and immersed in a silver nitrate solution. Sensors provided with a silver-backed, silver bromide membrane have been found to give a similar response to silver ion in a silver nitrate solution. Sensors provided with the silver-backed silver bromide membrane are also responsive to bromide ion in solution, and if immersed in a solution containing both bromide ion and silver ion will respond selectively to bromide ion.

For satisfactory operation in the apparatus of FIG. 2 it is essential that the response of the sensors be extremely stable; that is, if the output of one of sensors 1 increases even slightly, the process controller will interpret this as difference in ion concentration between reference solution 14 and test solution 15a and accordingly take corrective action.

Solid state membranes for use in practicing this invention are made by die pressing a layer of powdered specific ion sensing material together with a layer of metallic silver powder into a solid, impervious and intimately bonded mass. The specific ion sensing material may be either silver sulfide or silver bromide, and the silver powder should be used in sufficient amount to produce a bond line of the general type hereinafter described with reference to FIGS. 6 and 7. Longer operating life will be achieved with increasing amounts of silver, but the high cost of silver limits the practical thickness of the silver layer to something in the order of about 500 microns. As discussed below actual test data has shown high sensitivity and extremely long life for sensors employing membranes with a die pressed silver backing having an average thickness in the order of about 150 microns. The overall dimensions of the membrane are not critical, but a typical embodiment may have a diameter of about 13 millimeters and a thickness ranging from 0.5 to about 5.0 millimeters.

By way of example a silver/silver sulfide membrane may use as starting materials 400 mesh silver powder and silver sulfide powder having a purity of about 99.99%. Typically the silver sulfide powder may have a lead impurity of about 0.005% and smaller trace amounts of iron, manganese, and other elements. Preferably the silver powder is placed first in the die, which preferably should be of stainless steel construction, and the silver sulfide powder is placed on top thereof. For a membrane having a diameter of 15 millimeters there may be used about 0.2 grams of silver powder, and this powder is distributed into a fairly even layer on the bottom of the die. On the top of this may be evenly spread about 1.5 grams of the above mentioned silver sulfide powder. Thereafter the layered powders are pressed under a load of about 50 tons per sq. in. This may be accomplished in a hand hydraulic press having a ram surface which is machined flat and highly polished. The result is a liquid impervious silver sulfide membrane with a intimately bound silver layer on one side and a smooth shiny silver sulfide surface on the other. The membrane is prepared for further assembly by abrading the silver side with a number 320 grit paper.

Braided wires 6 are attached to silver plate 3 by means of a conductive epoxy. For this application the conductive epoxy should have a lap shear strength of about 800 psi, a flexural strength of about 12,000 psi, and a volume resistivity of about $2 \times 10^{-4}$ ohm-cm. A suitable product for this purpose is marketed by Emerson and Cuming Inc. under the name Eccobond 56C. This epoxy is provided together with a modified aliphatic amine catalyst. Braided wires 6 should be prepared for the bonding process by unbraiding them at the lower ends thereof and bending them outwardly at a 90° bend. Thereafter the epoxy is prepared, and the joint is made. The bond should be cured at room temperature for about 8 to 16 hours.

The next step in making the membrane subassembly is to apply non conductive coating 4. Coating 4 should be applied to a thickness of about 5 mils, and should cover the side edges of membrane 2, the side edges and back face of silver plate 3, and the lower end of braided wires 6. Any durable dielectric material may be used for this purpose. A number of suitable resinous coatings are commercially available, and typically come in two parts; one part being a polymer solution and the other a curing agent. The two solutions are simply mixed and painted upon the areas to be coated. Coatings which cure at room temperature in 8 to 16 hours have been found to be acceptable. Preferably the coating when cured should have a volume resistivity of at least about $10^{12}$ohm-cm., a dielectric strength of about 460 volts per mil, and a hardness of about 80 as measured on a Shore durometer. The coating should also be flexible and uneffected by thermal cycling between temperatures ranging from about $-70°$ to about $+300°$ F. An example of such a coating is Eccocoat VE produced by Emerson and Cuming Inc.

Housing 9 is made from a semi rigid, non conducting material such as unplasticized polyvinyl chloride. The material must be impervious to chemical solutions and create an excellent bonding surface for sealing the membrane subassembly. Housing 9 is prepared for reception of the membrane subassembly by abrading the receiving surface with a sand blast or vapor blast, and thereafter cleaning and degreasing the abraded area with toluene. Prior to final assembly, braided wires 6 are soldered to a long stranded wire. Thereafter the membrane subassembly is bonded in place within housing 9 with the long stranded wire extending out through the open end in the region of threads 12. The bonding agent should be a non conductive epoxy adhesive. Care should be taken that all air bubbles are evacuated from the epoxy prior to application (as by evacuation in a bell jar at a pressure of 2 cm Hg or less), and a good sealing joint should be obtained all around the coated edges of membrane 2. Any excess adhesive should be wiped from the front surface of the membrane. A room temperature cure is again effected for about 8 to 16 hours.

The final step in the sensor assembly is to snip off the end of the long stranded wire and solder the wire to pin jack 8. Thereafter an epoxy adhesive is applied to pin jack 8, and the pin jack is screwed into housing 9. For silver/silver bromide sensors a similar procedure is followed.

It is to be noted that the die pressing procedure employed for production of the solid state membrane is critical to the operation of this invention. As mentioned above the pressing of a layer of silver powder together with a layer of specific ion sensing powder provides a composite membrane with a layer of metallic silver intimately bonded to the specific ion sensing material. It is not known whether the nature of the bond line so achieved plays a direct role in the sensing process or whether it affects sensor performance indirectly by anchoring a silver layer of considerably greater thickness than could be achieved by other membrane production methods. However, sensors comprising membranes so produced have been found to be quite superior to similarly configured sensors comprising membranes having a vapor deposited silver backing.

It is believed that during operation of a sensor made in accordance with this invention, there is a continuous depletion of silver from the silver sulfide or silver bromide layer by the process solution and a continuous replenishment of this lost silver by the silver backing. This belief is supported by observation of what may be termed a "burn-out" phenomenon in the above mentioned sensors employing membranes having a vapor deposited silver backing. After about 3 months of continuous use the vapor deposited sensors begin giving erratic output signals. Inspection of the sensors after the onset of such erratic operation has shown that the silver in the central region of the backing layer has become depleted.

Sensors made in accordance with this invention may have a backing of almost any thickness desired, so that sensor life apparently could be increased almost indefinitely by merely increasing the amount of silver powder employed. However, an average thickness of about 150 microns is more than sufficient as tests of such sensors have shown no erratic operation or, silver burn-out, after 24 months of continuous use. It will be appreciated that burn-out of the vapor deposited membranes cannot thus easily be avoided because of the cost and impracticality of coating to a thickness much greater than about 1 micron.

As mentioned above, sensors made in accordance with this invention are particularly well suited for use in process controllers of the type as illustrated generally in FIG. 2 and described in detail in Ser. No. 235,116. In such controllers there is employed a reference solution and a process solution into which a pair of specific ion sensors are placed. The process controller takes a corrective action upon the basis of a difference signal derived from the two sensors. Accordingly it is essential for such operation that the one sensor not drift relative to the other. Thus when a sensor begins the erratic operation with which burn-out is associated, it must be replaced.

A series of tests of sensors having membranes with a vapor deposited silver backing have shown that in addition to burn-out there is an increasing sensor impedance associated with onset of erratic operation. Similar tests of sensors having a die pressed silver backing have shown neither erratic operation nor increasing sensor impedance, even after very long periods of use. The data from these tests are summarized in FIGS. 4 and 5.

FIG. 4 presents impedance data for a pair of silver/silver bromide sensors which were life tested in a recirculating ferri/ferrocyanide photographic bleach solution. The bleach solution was saturated with silver bromide and was maintained at 45° C. Data line A plots the measurements for a sensor having a membrane with a pressed silver backing, while data line B plots corresponding measurements for a sensor having a membrane with a vapor deposited silver backing. After 12 months of continuous operation the pressed silver device was still operating in a stable manner and was maintaining a constant impedance of about 10,000 ohms. In contrast the vapor deposited device began erratic operation after about only 1½ months. After 2 months the vapor deposited device was essentially useless for high accuracy ion sensing, and this performance degradation is seen to be associated with a sensor impedance which increases gradually from about 15,000 to about 33,000 ohms.

FIG. 5 presents similar data for a pair of silver/silver sulfide sensors. These tests were run for only 3 months. Again the sensor with the pressed silver membrane backing (data line C) maintained a constant impedance and continued reliable operation. Under the same conditions the sensor with the vapor deposited silver membrane backing (data line D) exhibited increasing impedance and erratic operation after about 2 months. It should be noted that in the case of these membranes the above mentioned photographic bleach solution was again used, but the sensors monitored silver ion. It will be appreciated that this measurement of silver ion by the silver sulfide sensor is in effect a measurement of bromide ion because of the solubility product of silver bromide.

Figure 6:
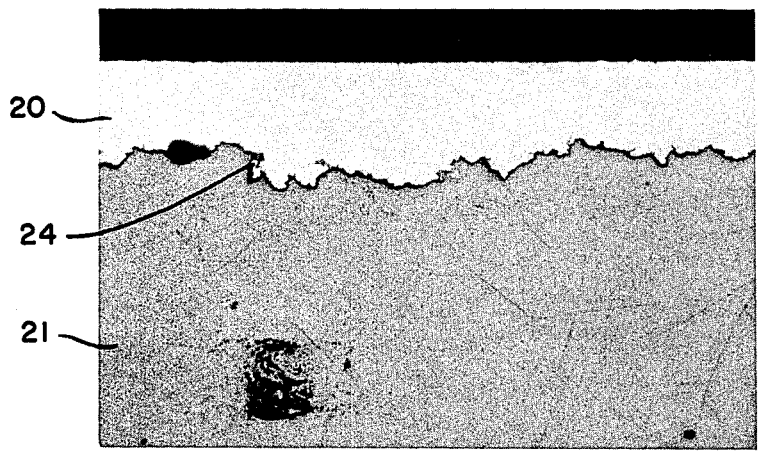
FIG. 6 is a photomicrograph at 250 × magnification of a silver bromide membrane having a die pressed silver backing.
Figure 7:
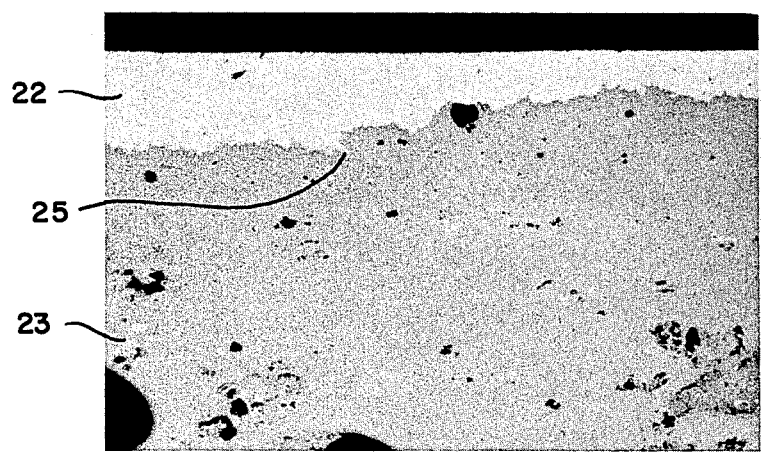
FIG. 7 is a photomicrograph at 250 × magnification of a silver sulfide membrane having a die pressed silver backing.

The physical construction of membranes such as those for which data lines A and C apply is shown in FIGS. 6 and 7 respectively. Each of these figures is a photomicrograph at 250 times magnification and each shows the bond line between the specific ion sensing material and the pressed silver backing. In FIG. 6 the silver backing is denoted by the reference numeral 20 and the silver bromide material by the reference number 21. In FIG. 7 the reference numerals 22 and 23 apply respectively to the pressed silver backing and the silver sulfide material. The dark line at the silver/silver bromide interface of FIG. 6 is merely a shadow and does not indicate any cleavage.

For both of the membranes illustrated it is seen that the specific ion sensing material and the silver backing have been intimately bonded into a single solid mass. In each case the membrane is about 13 millimeters in diameter by about 3 millimeters thick and has an average silver layer thickness of about 150 microns. As illustrated by FIGS. 6 and 7, the silver/silver bromide membrane appears to have a somewhat thicker silver backing than the silver/silver sulfide membrane. This, however, is a result only of the locations at which the sections were made and the care with which the layer of silver powder had been levelled prior to membrane pressing. Overall the illustrated membranes may be considered typical of membranes made for use in sensors of this invention.

It is seen that the bond line between the silver and the ion sensing material is exceedingly irregular so as to produce an exceptionally large contact area. Moreover the bond line even reverses direction occasionally as shown at 24 for the silver/silver bromide membrane and at 25 for the silver/silver sulfide membrane. Consequently there is a strong interlocking bond which resists any delaminating forces associated with normal operational use.

It will be readily apparent that the irregularity of the bond line causes point-to-point variation in silver layer thickness over and above the above mentioned variations due to uneven levelling within the mold. Measurements of such variations on a typical membrane have shown that the bond line irregularities generally produce a layer thickness variation of about 30 microns; that is, a well levelled layer of 150 microns average thickness can be expected ordinarily to vary in thickness from about 135 to about 165 microns, if the membrane is made strictly in accordance with the above procedure. This range, however, neglects occasional irregularities of unusual magnitude.

Strictly from a bonding point of view, the above mentioned membranes have a silver layer excess amounting to about 135 microns of thickness. That is, the bond lines could in theory exist in the configurations of FIGS. 6 and 7 for membranes having an average silver backing thickness of only about 15 microns. It is preferably, however, that the silver backing be somewhat thicker than this in order to provide excess silver for transfer into the silver bromide or silver sulfide layer during operation of the sensor.

The structure which is illustrated in FIGS. 6 and 7 is in sharp contrast to the structure of a membrane having a vapor deposited silver backing. On the scale of FIGS. 6 and 7 a 1 micron vapor deposited backing would show up only as a barely discernable line on the membrane surface. Such a backing is likely to have contaminating material under the silver and is unable to resist delaminating forces of any significant magnitude. Thus the backing tends to flake off easily under operating conditions or even during polishing in preparation for the making of photomicrographs.

While the method herein described, and the forms of apparatus for carrying this method into effect, constitute preferred embodiments of the invention, it is to be understood that the invention is not limited to this precise method and forms of apparatus, and that changes may be made in either without departing from the scope of the invention.

What is claimed is:

1. A specific ion sensor comprising:
    a. a housing,
    b. a membrane mounted in said housing, said membrane being produced by placing a layer of powdered specific ion sensing material selected from the class consisting of silver sulfide and silver bromide in a die in contact with a layer of powdered metallic silver and pressing said powder layers into a solid, impervious and intimately bonded mass with the silver portion thereof having an average thickness ranging between about 15 and 500 microns; the mounting of said membrane being such that said ion sensing material faces outwardly for contact with a process solution and said silver layer is electrically isolated from the exterior of the housing,
    c. an electrical terminal mounted in said housing for delivering a signal to an external instrument, and
    d. solid electrical connection means between said silver layer and said terminal.

2. A specific ion sensor according to claim 1 wherein the pressed silver layer comprising said membrane has an average thickness of about 150 microns.

3. A specific ion sensor according to claim 1 wherein said solid electrical connection is a braided wire.

4. A specific ion sensor according to claim 1 wherein said solid electrical connection is bonded to said silver layer by a conductive cement and further wherein the sides of said membrane, the surface of said silver layer, and the bond area between said electrical connection means and said silver layer are all covered by an insulative coating.

5. A specific ion sensor according to claim 1 wherein said housing is exteriorly threaded at the end remote from said membrane for releasible physical connection to an associated electrical instrument and said electrical terminal is a pin jack for electrical connection to said instrument.

6. A specific ion sensor comprising:
    a. a membrane subassembly comprising
        1. a solid state membrane produced by die pressing a backing layer of powdered silver against a layer of powdered specific ion sensing material selected from the class consisting of silver sulfide and silver bromide, said pressing being continued until said powder layers are transformed into a solid, impervious and intimately bonded mass with the silver portion thereof having a thickness ranging between about 15 and 500 microns,
        2. a first connecting wire bonded to said backing layer by a conductive epoxy, and
        3. a non conductive epoxy coating extending over said backing layer, the portions of said first connecting wire contacting and adjacent said backing layer, and the sides of said membrane; and b. a housing subassembly comprising:
  1. a non conductive housing provided with a membrane receiving seat at one end thereof and an internal channel extending from said seat to the opposite end of said housing,
  2. an electrical terminal mounted at said opposite end, and
  3. a second connecting wire bonded to said terminal and extending down the length of said channel; said membrane subassembly being bonded to said housing with said membrane being sealed in place within said seat and said first connecting wire being bonded to said second connecting wire.

7. A method of making a specific ion sensor comprising the steps of:
  1. placing into a die mold a layer of powdered specific ion sensing material selected from the class consisting of silver sulfide and silver bromide,
  2. placing a layer of powdered metallic silver into said die mold in contact with said layer of specific ion sensing material,
  3. pressing said powder layers in said mold to obtain an impervious, silver-backed solid state membrane with the backing having an average thickness ranging between about 15 and 500 microns,
  4. bonding a connecting wire to said silver backing,
  5. coating said silver backing and the sides of said membrane with an insulative material,
  6. sealing said membrane in a housing provided with an electrical terminal, and
  7. connecting said connecting wire to said terminal.

8. A method according to claim 7 wherein said pressing is carried out under a pressure of about 50 tons per sq. in.

9. A method according to claim 7 wherein said silver power is about 12 percent by weight of the total powder placed in said mold.

* * * * *